(12) United States Patent
Hara et al.

(10) Patent No.: US 8,034,581 B2
(45) Date of Patent: Oct. 11, 2011

(54) CELL-FREE EXTRACT AND GLYCOPROTEIN SYNTHESIS SYSTEM

(76) Inventors: Toshio Hara, Fukuoka (JP); Hiroshi Tarui, Fukuoka (JP)

( * ) Notice: Subject to any disclaimer, the term of this patent is extended or adjusted under 35 U.S.C. 154(b) by 0 days.

(21) Appl. No.: 10/303,090

(22) Filed: Nov. 25, 2002

(65) Prior Publication Data

US 2003/0157594 A1    Aug. 21, 2003

Related U.S. Application Data

(60) Provisional application No. 60/332,559, filed on Nov. 26, 2001.

(51) Int. Cl.
*C12P 21/06* (2006.01)

(52) U.S. Cl. ...................................................... 435/68.1
(58) Field of Classification Search .................. 435/68.1
See application file for complete search history.

(56) References Cited

U.S. PATENT DOCUMENTS

| 5,324,637 A | * | 6/1994 | Thompson et al. | 435/68.1 |
| 5,492,817 A | * | 2/1996 | Thompson et al. | 435/68.1 |
| 5,643,722 A | * | 7/1997 | Rothschild et al. | 435/6 |

FOREIGN PATENT DOCUMENTS

| JP | 2000-325076 A | 11/2000 |
| JP | 3713402 B2 | 11/2005 |

OTHER PUBLICATIONS

Popov, M. et al., "Mapping the Ends of Transmembrane Segments in a Polytopic Membrane Protein", 1997, J. Biol. Chem., vol. 272: pp. 18325-18332.*
Lux, S. et al., "Cloning and characterization of band 3, the human erythrocyte anion-exchange protein (AE1)", 1989, PNAS, vol. 86: pp. 9089-9093.*
Duszenko, M. et al., "In vitro translation in a cell-free system from *Trpanooma brucei* yields glycosylated and glycosylphoshphatidylinositol-anchored proteins", Eur. J. Biochem., 1999, vol. 266: pp. 789-797.*
Tarui, Hiroshi et al., "Establishment and characterization of cell-free translation/glycosylation in insect cell (*Spodoptera frugiperda* 21) extract prepared with high pressure treatment," Appl. Microbiol. Biotechnol. 55: 446-453 (2001).
Tarui, Hiroshi et al., Insect Cell Extract Preparation by the Nitrogen Disruption Method for Cell-Free Translation, J. Fac. Agr., Kyushu Univ., 45 (1): 135-148 (2000).
Tarui, Hiroshi et al., "A Novel Cell-Free Translation/Glycosylation System Prepared from Insect Cells," Journal of Bioscience and Bioengineering, 90 (5): 508-514 (2000).

* cited by examiner

*Primary Examiner* — Michael Burkhart

(57) ABSTRACT

Insect cells are stored in a small gas cylinder, and the small gas cylinder is charged with nitrogen gas to pressurize the cylinder. The charged gas is exhausted at once to crush the cells to provide the objective cell extract with translation activity and glycosylation activity. As this method is gentler than the conventional cell-crushing method employing a homogenizer, in addition to translation factors, factors carrying glycosylation activity can also be recovered. As a result, an in-vitro glycoprotein synthesis system capable of performing translation to post-translation glycosylation can be produced.

1 Claim, 17 Drawing Sheets

F I G. 1
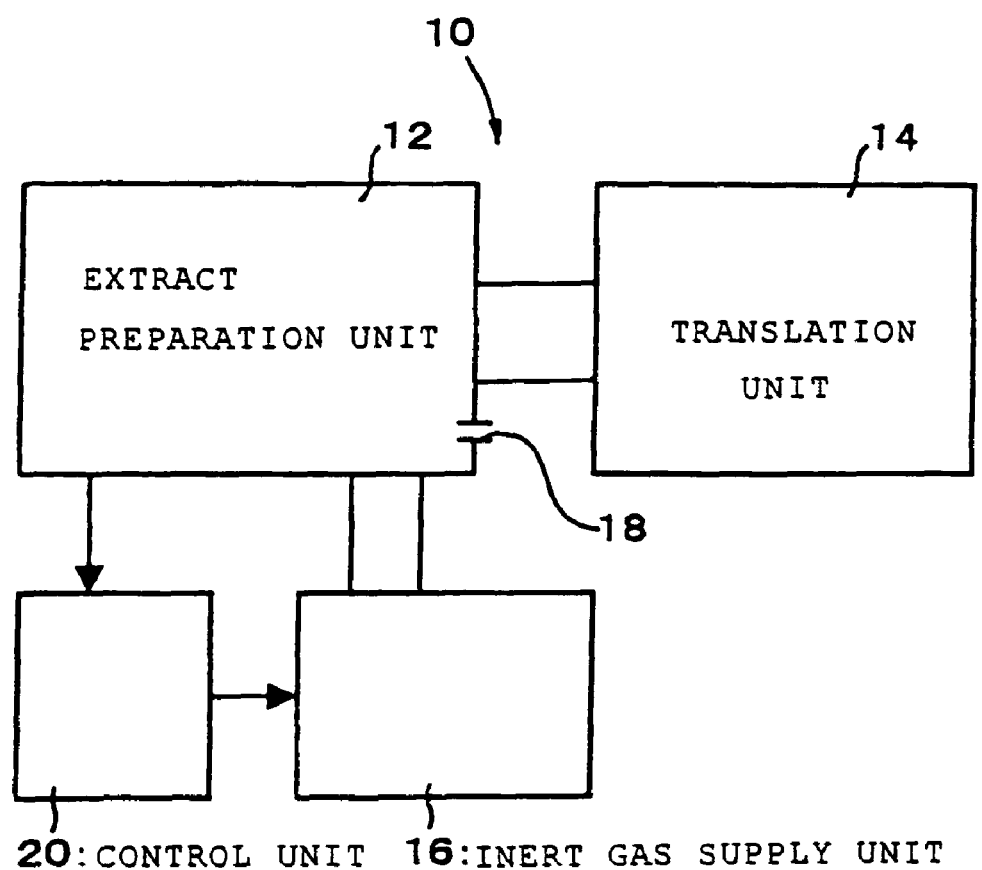

FIG. 3

GGGA▒▒▒▒AUG               UAA▒▒▒▒CTGCA
POLYHEDRIN 5'-UTR    *gp120*    POLYHEDRIN 3'-UTR
     52base         1509 base       379base

FIG. 4

|  | GP120 | | | | | |
|---|---|---|---|---|---|---|
| mRNA | − | + | − | + | − | + |
| GAS PRESSURE (kg/cm²) | 5 | | 8 | | 14 | |
| LANE NO. | 1 | 2 | 3 | 4 | 5 | 6 |

①→

②→

(1) GLYCOSYLATED GP120

(2) UNGLYCOSYLATED GP120

F I G. 5
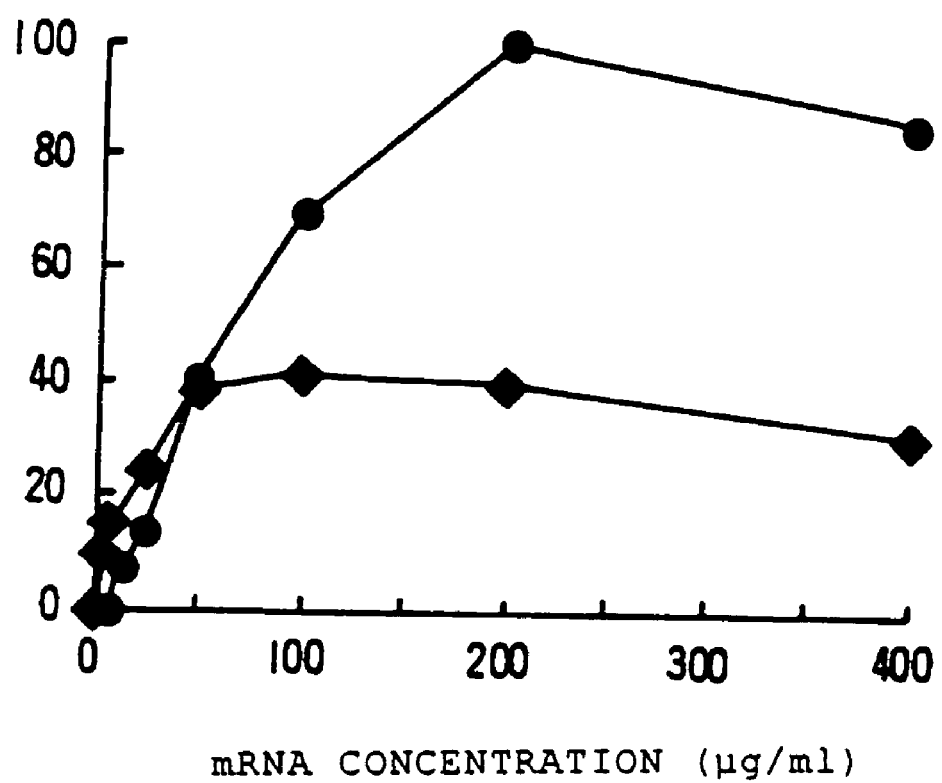

F I G. 9
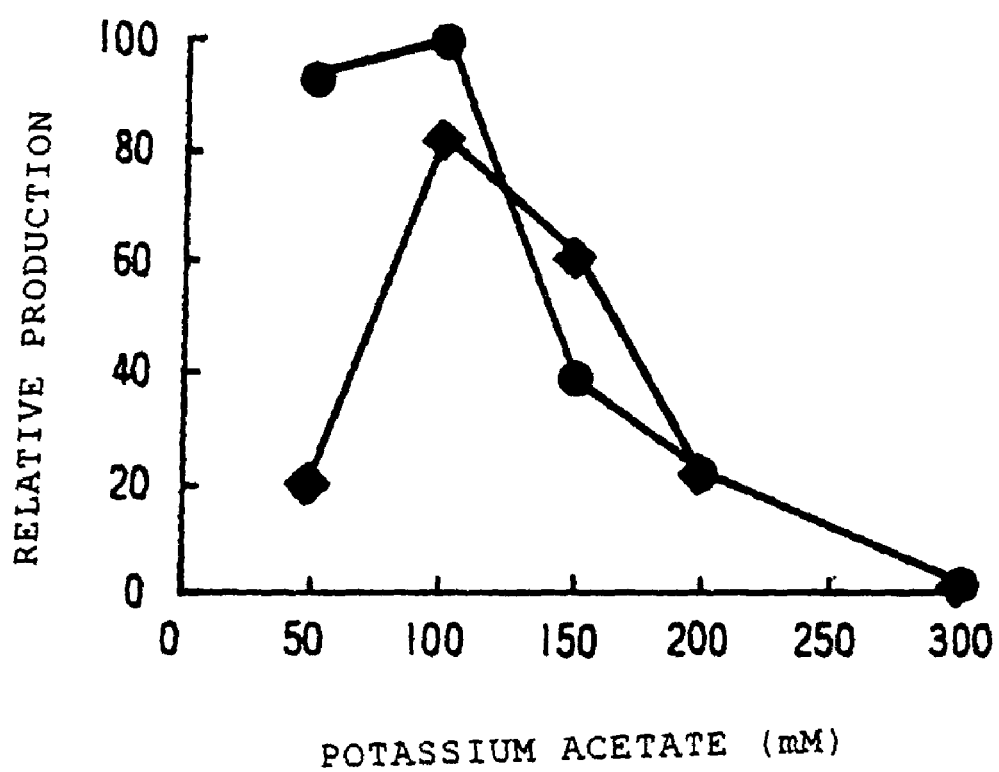

F I G. 1 6
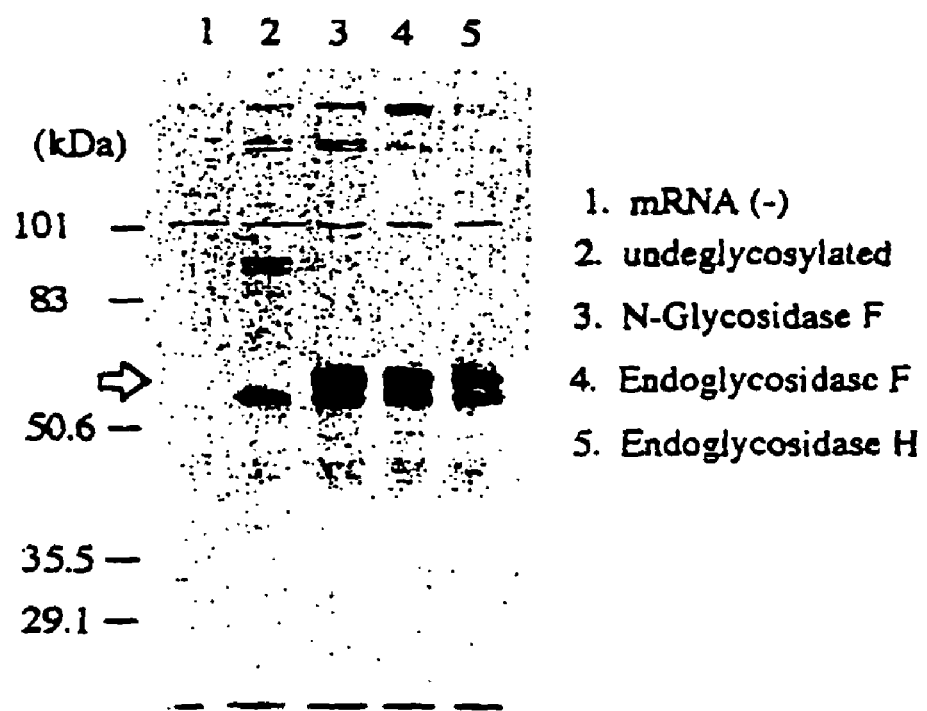

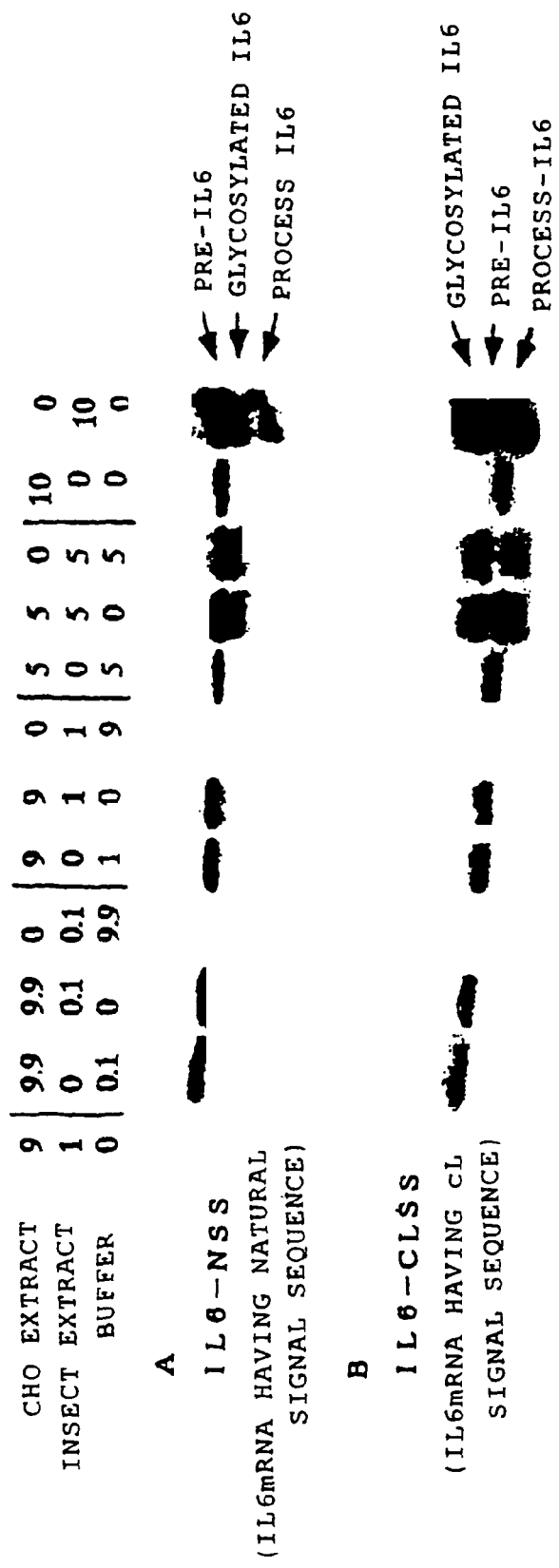

CELL-FREE EXTRACT AND GLYCOPROTEIN SYNTHESIS SYSTEM

BACKGROUND OF THE INVENTION

1. Field of the Invention

The present invention relates to an in-vitro translation system capable of extracellularly synthesizing protein by employing a cell extract, and particularly to a system capable of implementing both protein synthesis and glycosylation, to synthesize glycoprotein from the cell extract.

2. Description of the Related Art

Functional information within living organisms is recorded on nucleic acids. Proteins (which are functional molecules) are translated, and functional RNA molecules (ribozymes for example) are transcribed, using this nucleic acid as the template. In recent years, analysis of nucleic acid and protein supporting biofunction has been actively conducted, and development of analyzing methods and analyzing means has also been promoted.

Methodology for analyzing nucleic acid has particularly shown impressive progress pursuant to the development of a polymerase chain reaction (PCR) and the like. According to PCR, by adding a primer and template DNA in a cell-free reaction solution containing polymerase enzymes, it is possible to freely amplify DNA fragments of template DNA. In other words, the nucleic acid can be freely synthesized and amplified extracellularly. The synthesized nucleic acid can be, for example, used to determine the primary structure (base sequence), and it is thereby possible to accelerate the progress of nucleic acid analysis, such as genome analysis.

Meanwhile, with respect to methodology for analyzing protein, various cell-free translation systems have been developed since A. S. Spirin, et al., developed an in-vitro protein synthesis system employing *E. coli* extract. In addition to the aforementioned *E. coli*, there are cell-free translation systems which utilize other material, for example, cell extracts prepared from wheat germ, rabbit reticulocyte, and so on.

Among the above, the more general cell-free translation system deriving from wheat germ grinds the wheat germ together with glass beads, a mortar, or the like and synthesizes protein from mRNA by employing the cell extract obtained from such ground wheat germ. In other words, it is possible to recover the cell extract from wheat germ while preserving the protein synthesis (translation) activity existing in the wheat germ, and protein may be freely synthesized extracellularly by employing such recovered cell extract.

If protein can be freely synthesized extracellularly as described above, it becomes possible to obtain a desired protein easily by eliminating complex factors and complications that accompany synthesizing the protein in cells, and this is advantageous in terms of analyzing the protein. From the foregoing perspective, improvement of cell-free translation systems has been conducted heretofore, and such technology is disclosed, for example, in Japanese Patent Publication No. H1-503119, Japanese Patent Laid-Open Publication No. H4-200390, Japanese Patent Laid-Open Publication No. H7-203984, among others. Moreover, such cell-free translation systems are commercially available as kits (Amasham, etc.) and are widely available.

Nevertheless, although the conventional cell-free translation systems described above are capable of performing translation to the protein, there is a problem in that they are not able to perform post-translational modification of the translated protein. In other words, it is known that many of the intracellular proteins are translated as protein based on the mRNA transcribed from the template nucleic acid, and modified after such translation. Glycosylation is one such post-translational modification.

The sugar chain added pursuant to post-translational glycosylation is considered to function as a signal or ligand relating to the recognition or adhesion between substances or cells, as a function-adjusting factor of the protein itself, or as a protective or stability factor of the protein. Thus, in order to analyze the function within living organisms with respect to the protein being glycosylated, it is necessary to obtain such a glycosylated protein.

This glycosylation adds a sugar chain to a specific amino acid of the protein. Since the glycosylation reactions differ variously and are complicated, it is not easy to chemically add a sugar chain to a protein synthesized with the foregoing cell-free translation systems.

In view of such a problem, a currently available biochemical method, for example, derives an extract having glycosylation activity from dog tissue and uses the extract to add a sugar chain to protein from a cell-free translation system. The extract having glycosylation activity is prepared by crushing the dog tissues with a homogenizer and recovering microsome fractions containing a Golgi body by centrifugation.

This dog tissue extract, however, is used separately from conventional cell-free translation systems. Specifically, protein is synthesized with a cell-free translation system, and, after having recovered the synthesized protein, glycosylation is performed thereto by transferring the synthesized protein to such dog tissue extract. As a result of this acquirement of dog tissue extract, the extracellular biochemical synthesis of glycoprotein became possible. And, by employing this synthesized glycoprotein for the likes of protein performance analysis, analysis capable of further reflecting the intercellular reaction, as opposed to protein synthesized with a conventional cell-free translation system in which glycosylation has not been performed thereto, is anticipated.

Nevertheless, with the glycoprotein synthesis employing the conventional dog tissue extract, glycosylation is conducted after recovering the protein that has been synthesized with a conventional cell-free translation system. As described above, synthesis of glycoprotein through separate use of a cell-free translation system and a glycosylation system is not preferable in proteins that generally denature easily, and it is also possible that this will lead to deterioration in activity. Further, in addition to the physical influence on the protein, people working with such proteins have to concentrate on preparing the aforementioned two systems and synthesizing glycoprotein in two stages, thus making the procedure complicated.

Moreover, with respect to a cell extract capable of performing glycosylation, only those deriving from a restricted tissue such as dog tissue can be used at present, and it is not yet possible to recover a glycosylation activity from universal tissue cells. The type of sugar chain will differ depending on the type of cell, and it is anticipated that the glycosylation reaction will differ depending on such cell type. Therefore, protein glycosylation can be freely designed if the recovery of glycosylation activity from various cells becomes possible.

Furthermore, in recent years, various protein preparations have been developed in the medical field, and it is known that the effect of such preparations is influenced by the existence or type of sugar chain of the constituent protein. Thus, the realization of recovery of glycosylation activity from various cells is anticipated to also contribute significantly to the development and improvement of such protein preparations.

Therefore, in view of the foregoing problems, the inventors of the present application conducted intense study regarding the preparation of a cell extract capable of conducting a series of processes from protein synthesis to glycosylation within a single system, and, through this research, they realized a novel preparation of a cell-free extract differing from a conventional cell-free translation system, and enabled the series of processes from protein synthesis to glycosylation to be conducted within a single system by employing such extract.

SUMMARY OF THE INVENTION

Accordingly, as a result of examining the preparation of a cell extract, inventors of the present invention realized the preparation of the cell extract described below. In one embodiment of the cell extract preparation of the present invention, the cells are crushed with a gentle means of changing the pressure surrounding the cells from pressurization to depressurization, and, at the least, the protein synthesis activity and glycosylation activity of the cells in the cell extract are recovered.

In other words, one embodiment of the cell extract of the present invention is a cell-free extract prepared by crushing cells and which has activity for synthesizing protein from a template nucleic acid, wherein the cells under pressure are depressurized and thereafter crushed in an inert gas atmosphere.

In another embodiment of the present invention, the cells are prepared through crushing or disrupture pursuant to a pressure change without grinding the cells as with conventional homogenizers. By crushing the cells pursuant to a pressure change as described above, as opposed to conventional cell-crushing methods employing a homogenizer, the cells can be crushed under gentle conditions and it is thereby possible to reduce damage to intracellular organs.

In an embodiment of the present invention, the cells are animal cells.

In another embodiment of the present invention, an inert gas flow is supplied and pressurized in the atmosphere, and the inert gas is exhausted from the atmosphere and depressurized thereafter.

In an alternative embodiment of the present invention, the inert gas is nitrogen, carbon dioxide or argon.

In yet another embodiment of the present invention, the inert gas is supercritical gas.

Another embodiment of the cell extract of the present invention is a cell-free extract prepared by crushing cells having a protein synthesis activity and a glycosylation activity for adding a sugar chain to the synthesized protein, and which is capable of synthesizing glycoprotein from a template nucleic acid, wherein the cells under pressure are depressurized and crushed in an inert gas atmosphere so as to preserve the protein synthesis activity and glycosylation activity of the cells.

According to an embodiment of the present invention, by crushing the cells having a protein synthesis (translation) activity and glycosylation activity pursuant to a pressure change so as to avoid destroying both such activities, it is possible to prepare a cell extract retaining both activities. It is thereby possible to create a system having both a cell-free translation system and a glycosylation system, which were conventionally prepared separately, and, by using such a system, protein synthesis and glycosylation can be implemented with a single cell extract.

In an alternative embodiment of the present invention, the cells derive from insects.

In an embodiment of the present invention, an inert gas flow is supplied and pressurized in the atmosphere, and the inert gas is exhausted from the atmosphere and depressurized thereafter.

In yet another embodiment of the present invention, the inert gas is nitrogen, carbon dioxide or argon.

In an alternative embodiment of the present invention, the pressure at the time of pressurization is 2 to 14 $kgf/cm^2$.

In another embodiment of the present invention, the cells are crushed in a state of being prepared at 0.25 to $1.5 \times 10^8$ cells/ml.

The present invention also provides a cell-free glycoprotein synthesis composition. An embodiment of this cell-free glycoprotein synthesis composition is formed by adding a cell extract having the foregoing glycosylation activity to the cell extract having the protein synthesis activity. As described above, by supplementing a glycosylation activity through the addition of a cell extract having a glycosylation activity to a cell extract which only has a protein synthesis activity on its own, it is thereby possible to compose a composition having both the protein synthesis activity and the glycosylation activity.

In an embodiment of the present invention, the cell extract having the protein synthesis activity is prepared by depressurizing cells under pressure and crushing the cells in an inert gas atmosphere.

The present invention also provides a glycoprotein synthesis system. One embodiment of this glycoprotein synthesis system comprises mRNA synthesizing means for transcribing mRNA from a DNA coding protein capable of being glycosylated. The embodiment also comprises glycoprotein synthesizing means capable of synthesizing glycoprotein from such synthesized mRNA pursuant to a cell-free extract or composition having the protein synthesis activity and glycosylation activity. The glycosylated glycoprotein is synthesized with the glycoprotein synthesizing means based on the mRNA transcribed from the DNA with the mRNA synthesizing means.

In one embodiment of the system of the present invention, so as long as a template DNA is prepared in advance, glycoprotein can be easily synthesized from this template DNA via the mRNA.

Other embodiments of the glycoprotein synthesis system may further comprise an expression vector for expressing mRNA from the DNA by inserting, into a position downstream of a promoter, the DNA coding the protein capable of being glycosylated. By further comprising an expression vector as described above, for example, it becomes possible to easily synthesize glycoprotein by removing a gene of interest from the genome and connecting such gene to this expression vector.

In an embodiment of the present invention, this expression vector is provided with an untranslated region sequence. The untranslated region sequence adds an untranslated region sequence to the mRNA synthesized pursuant to expression from the promoter and derives from the gene for a protein capable of being glycosylated inside the cells used to prepare the cell-free extract. By providing an untranslated region of a gene that produces glycoprotein inside the cells as described above, it becomes possible to improve the efficiency of glycosylation to the synthesized protein.

In another embodiment of the present invention, the cells are insect cells, and the promoter and untranslated region within the expression vector may derive from a virus having insect cells as its host.

In one embodiment of the present invention, the virus is baculoviridae, and the promoter and untranslated region sequence may derive from baculoviridae polyhedrin.

Moreover, since glycoprotein can be produced easily through use of the cell-free extract, composition and glycoprotein synthesis system according to the present invention, intracellular performance analysis employing glycoprotein may be conducted with ease.

The present invention also provides a protein produced by employing the cell-free extract described above.

The present invention further provides a glycoprotein produced by employing the cell-free extract described above.

The present invention additionally provides a cell-free extract manufacturing device. This cell-free extract manufacturing device is for manufacturing a cell-free extract capable of synthesizing protein from a template nucleic acid by crushing cells having a protein synthesis activity, and comprises: a container for containing the cells; a gas supply unit for filling the container with inert gas; and a pressure control unit for pressurizing, and thereafter depressurizing, the pressure inside the container so as to enable the crushing of cells inside the container in a state of preserving the protein synthesis activity of the cells.

Moreover, in some embodiments of this cell-free extract manufacturing device, the cells further have a glycosylation activity for adding a sugar chain to the synthesized protein, wherein the pressure control unit pressurizes, and thereafter depressurizes, the pressure inside the container so as to enable the crushing of cells inside the container in a state of preserving the protein synthesis activity and glycosylation activity of the cells.

By employing these cell-free extract manufacturing devices, it is possible to easily manufacture a cell extract having a protein synthesis activity or a cell extract also having a glycosylation activity.

The present invention also provides a cell-free protein synthesis system. In an embodiment of the present invention, the cell-free protein synthesis system synthesizes unglycosylated protein by employing the foregoing cell-free extract and by using mRNA transcribed from the template DNA in which the intracellular transitional signal of the gene DNA corresponding to the glycoprotein has been deleted.

As described above, according to the present invention, it is possible to delete the intracellular transitional signal since the protein is synthesized with a cell-free system. With conventional methods of synthesizing protein without glycosylation, it was necessary to replace the amino acid of an N-type glycosylation signal and express it as a secretory protein outside the cell by employing an expression system such as —CHO cells, yeast or silkworm larva. When converting the N-type glycosylation sequence with amino acid replacement upon employing this type of expression system, there is a possibility that the three-dimensional protein structure will differ from the original structure thereof. Contrarily, according to the present invention, the elimination of a signal sequence at the DNA level becomes possible as a cell-free system is employed, and the identical protein structure can be adopted since a mature protein is synthesized without having to change the amino acid structure of the structural gene.

BRIEF DESCRIPTION OF THE DRAWINGS

FIG. 1 is a structural diagram of an embodiment of the translation device;

FIG. 3 is a structural diagram of the mRNA expressed with the expression vector in Example 1;

FIG. 4 is a diagram showing the examination results of the gas pressure conditions upon preparing the cell extract in Example 3;

FIG. 5 is a diagram showing the examination results of the additive amount of mRNA in Example 3;

FIG. 9 is a diagram showing the examination results of the potassium acetate concentration in Example 3;

FIG. 16 is a diagram showing the results of deglycosylation of the translational reaction product pursuant to the insect cell extract in Example 4; and FIG. 17 is a diagram showing the results of Western blotting upon analyzing the translation and glycosylation activity of the CHO-insect compositional solution in Example 7.

DETAILED DESCRIPTION OF THE EMBODIMENTS

Figure 2:
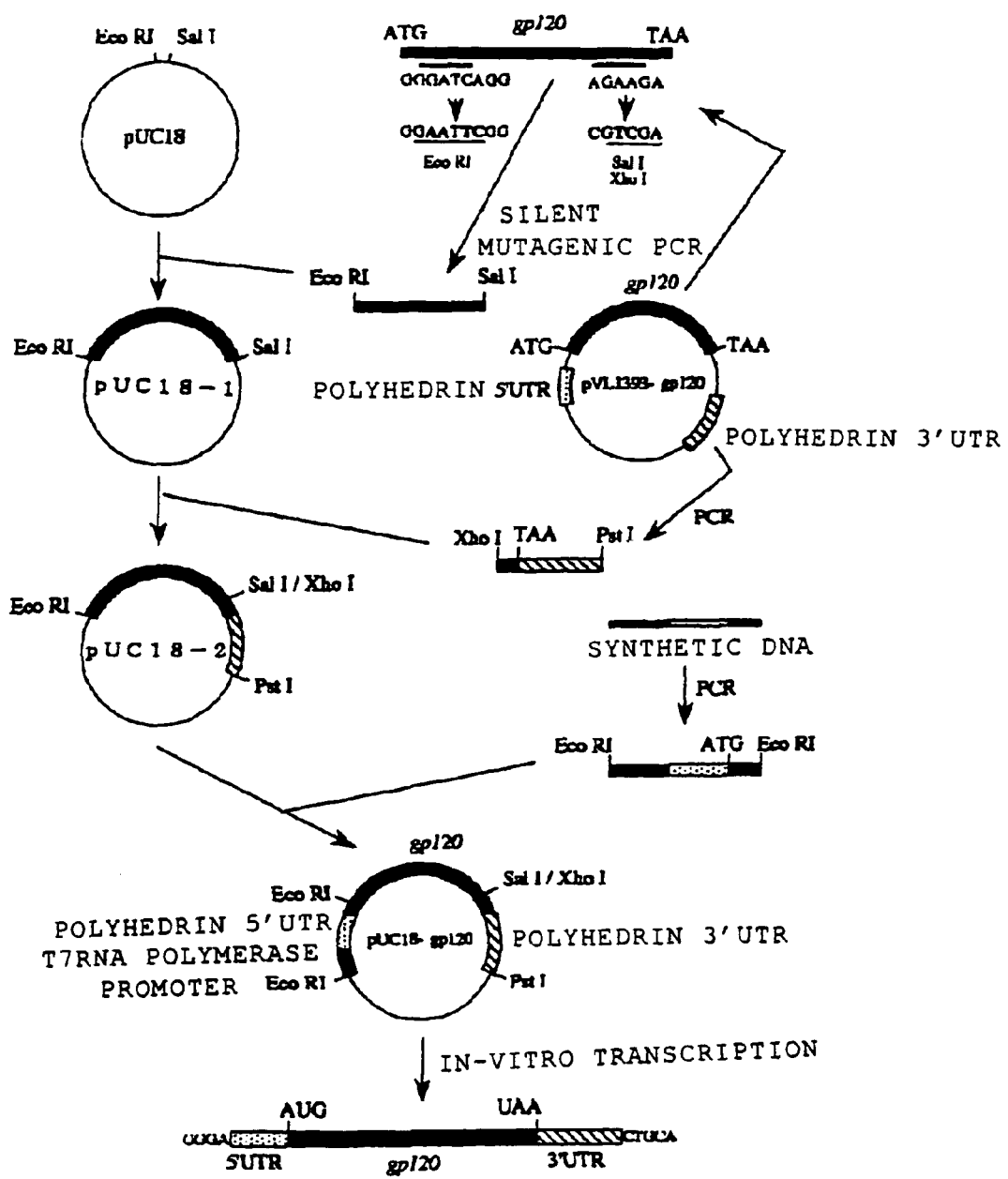
FIG. 2 is a diagram showing the construction method of the mRNA expression vector in Example 1.

Illustrative embodiments of the present invention are now explained.

Preparation of Cell-Free Extract

In one embodiment of the present invention, the cell-free extract is prepared by depressurizing cells under pressure and crushing such cells in an inert gas atmosphere.

Cells which may be used to prepare the foregoing cell-free extract may be any cells so as long as such cells have a translation activity for synthesizing protein from a template nucleic acid, and a glycosylation activity for implementing post-translation glycosylation, and may broadly include prokaryotic cells to eukaryocyte cells. For instance, cells of mammals, birds, reptiles, amphibians, fishes, plants, and microorganisms, among others, may be used. Among such aforementioned wide variety of cells, mammalian cells and insect cells may be preferably adopted as cells capable of recovering translation activity. Moreover, insect cells may be preferably adopted as cells for recovering both the translation activity and glycosylation activity. Further, these cells may be cells in tissues or obtained from tissues, or cultured cells.

In another embodiment of the present invention, these cells are disposed in an inert gas atmosphere while they are being crushed. This inert gas is used so that the extract after the crushing of cells will not influence the translation activity or the like upon contacting the air. Therefore, so as long as this objective can be attained, there is no limitation on the type of inert gas, and, for example, nitrogen or argon may be used.

The pressure at the time of pressurizing and crushing the cells may be suitably determined depending on the type of cells. This pressure may be determined, with the translation activity of the ultimately obtained extract as the index, upon giving consideration to the durability of factors relating to the strength of the film or wall covering the periphery of the cells to be used, internal translation, post-translation modification, and so on. For example, in some embodiments for cells deriving from insects, the pressure may be set to 2 to 14 kgf/cm$^2$, preferably to 5 to 8 kgf/cm$^2$, and more preferably to 8 kgf/cm$^2$. Moreover, in the case of an alternative embodiment for CHO cells, it is preferable that a pressure relatively higher than the insect cells be set, and, specifically, the pressure may be set to 2 to 32 kgf/cm$^2$. Further, the pressurization time may also be suitably determined pursuant to the various types of cells and so on. The pressurization time may be determined with the translation activity of the ultimately obtained extract as the index, taking into account relevant factors, such as those relating to durability or strength of the film or wall covering the periphery of the cells to be used, internal translation, post-translation modification, and so on. For example, in an embodiment for cells deriving from insects, such time may be set to 3 to 120 minutes, preferably to 30 to 120 minutes, and more preferably to 60 to 90 minutes.

In other embodiments of the present invention, the depressurization after pressurization will suffice so as long as the pressure is depressurized rapidly so as to enable the crushing of cells, and the pressure after depressurization may be set to a normal pressure or to a pressure lower than a normal pressure by mechanically lowering such pressure.

The pressure change from the aforementioned pressurized state to the depressurized state may be conducted, for example, by supplying and exhausting gas in and out of the atmosphere which contains the cells, or by contracting or expanding the volume of the contained cells. The inert gas described above may be preferably used in the former case of supplying and exhausting gas.

Ultimately, a cell-free extract is prepared by recovering the extract after the crushing of cells. This cell-free extract, in principle, is substantially identical to the cell extract within viable cells, and the existence of cell residue after the crushing is irrelevant. Therefore, the cell extract after crushing may be made into a cell-free extract in a state where residue exists, or after eliminating the crushed cell residue by centrifugation or the like as necessary.

Moreover, with respect to the cell-free extract prepared in an embodiment of the present invention, although an extract deriving from a specific cell may be used independently, there may be cases where the glycosylation activity is low or cannot be exhibited when independently using an extract deriving from a specific cell, even though it may possess protein synthesis activity. In such a case, it is possible to supplement the glycosylation activity by adding a suitable ratio of a cell-free extract deriving from other cells having glycosylation activity. For example, in an embodiment with the cell-free extract deriving from CHO cells that have protein synthesis activity but cannot exhibit glycosylation activity when used independently, a cell-free extract deriving from insect cells having glycosylation activity may be suitably added in order to supplement the glycosylation activity.

Glycoprotein Synthesis System

Next, an embodiment of the present invention wherein the template nucleic acid to be the substrate for performing translation and glycosylation upon employing the aforementioned cell-free extract is explained.

1. Expression Vector

For protein synthesis (translation), an mRNA as the template thereof is required, and for the production (transcription) of this mRNA, a DNA as the template thereof is required. Here, an expression vector containing the template DNA to be the substrate of mRNA synthesis is described.

A desired sequence coding the protein is inserted into the expression vector in order to synthesize the mRNA to become the substrate of protein synthesis. This protein code sequence is not particularly limited. One may use as this protein code sequence, for example, a sequence coding a protein capable of being glycosylated in order to enable the aforementioned cell-free extract to perform glycosylation after the protein synthesis.

In one embodiment of the foregoing expression vector, a promoter for commencing the transcription is provided to the upstream of the sequence coding the aforementioned protein. Although this promoter is not particularly limited, various RNA polymerase promoters, for example, may be used for synthesizing a single-strand mRNA, including a T7RNA polymerase promoter, T3RNA polymerase, SP6RNA polymerase and so on.

In alternative embodiments, 5' and 3' untranslated region (UTR) sequences are provided at both ends of the expression vector so as to sandwich the protein code sequence described above. These sequences are added as UTR at both ends of the mRNA upon being synthesized as mRNA and control the translation thereof. Since this UTR sequence functions as a control sequence upon conducting translation with the cell-free extract, it is preferable that this sequence is selected in accordance with the cells used in the preparation of the cell-free extract. For example, an alternative embodiment may use a UTR deriving from such cells or a UTR deriving from a virus or phage which infects such cells.

In an embodiment of the present invention, when employing insect cells for the preparation of the cell-free extract described above, a UTR deriving from insect cells or a UTR deriving from a virus (baculoviridae for instance) capable of infecting the insect cells may be used as the UTR thereof.

In yet another embodiment of the present invention, it is preferable that the expression vector described above retains an auto-reproduction performance. The auto-reproduction performance of various plasmids or virus DNA, for example, may be used for this type of auto-reproduction performance. These may be suitably selected in accordance with the host for amplifying the expression vector or with the host for realizing the expression pursuant to this vector. When selecting *E. coli* as the host, a pUC or pBR plasmid, for example, may be used as the expression vector. When selecting mammalian cells as the host, virus DNA such as SV40, for example, may be used. If necessary, a plurality of auto-reproduction performances may be provided in order to structure a shuttle vector having an auto-reproduction performance in differing hosts.

2. mRNA Synthesis

In order to synthesize mRNA with the expression vector described above, a transcription factor such as RNA polymerase is necessary. The transcription factor may be, among other things, provided in viable cells that retain a transcription factor. In other words, mRNA may be synthesized, for example, by inserting such viable cells in the aforementioned expression vector and employing the intracellular transcription factor. The mRNA synthesized here may be prepared as a target mRNA by being separated from other intracellular mRNA and refined thereafter in accordance with well-known methods.

When utilizing the intracellular transcription factor as described above, it becomes necessary to refine the target mRNA from numerous intracellular mRNA. In order to simplify the refining operation of such mRNA, this transcription factor may employ an extract having a transcription activity obtained from cells, and an in-vitro transcription system. Some examples of this in-vitro transcription system are a transcriptional reaction system deriving from T7 phage or a transcriptional reaction system deriving from E. coli. mRNA synthesis employing this system may be conducted upon utilizing commercially available kits, for instance, MEGAscript™ (Ambion), RiboMAX™ (Promega), and so on.

When performing mRNA synthesis (transcription process) in-vitro as described above, the series of processes from the mRNA synthesis (transcription) process to the protein synthesis (translation) described later and the glycosylation process thereafter may be implemented extracellularly, that is, in-vitro.

3. Translation and Glycosylation of Protein

In principle, the in-vitro translation and glycosylation reaction may be implemented by adding the aforementioned mRNA to the cell-free extract having both the protein synthesis activity and glycosylation activity. In other words, since the foregoing cell-free extract system has both the translation activity for protein synthesis and post-translational glycosylation activity, protein is synthesized from this mRNA pursuant to the addition of mRNA to the aforementioned cell-free extract system, and, thereafter, glycoprotein is synthesized by glycosylation being performed to this protein.

Moreover, upon synthesizing glycoprotein as described above, further cell extracts may be prepared by adding the likes of magnesium acetate, potassium acetate, spermidine, GTP, ATP, creatine kinase, buffer or the like. As an example, in a cell extract of insect cells, the translational reaction may be provided by setting the ultimate concentration to 10.6 mM HEPES-KOH (pH7.95), 1.3 mM magnesium acetate, 100 mM potassium acetate, 2.5 mM DTT, 0.25 mM spermidine, 444 µg/ml creatine kinase, 8.0 mM creatine phosphate, 1.2 mM ATP, and 0.25 mM GTP. Moreover, it is preferable to add an amino acid mixture to the extract. This mixture may be added, for example, such that the final concentration will become roughly 25 µm.

Further, although it is necessary to add mRNA to the cell extract to perform protein synthesis, this additive amount may be an additive amount similar to a conventional in-vitro translation system and, for example, may be added to the cell extract such that the final concentration becomes 200 µg/ml. With respect to protein synthesized pursuant to such a method, after being isolated from the cell extract as necessary, such synthesized protein (or glycoprotein) may be used for various purposes.

Translation Device

Preparation of the aforementioned extracts for the synthesis of protein (glycoprotein) may be automated. An embodiment of a device of the present invention for achieving such automation is depicted in FIG. 1. In the embodiment depicted in FIG. 1, a translation device 10 comprises an extract preparation unit 12 for preparing a cell-free extract from cells and a translation unit 14 for performing protein synthesis with the obtained extract.

This extract preparation unit 12 internally houses cells, the cells are crushed therein, and an extract is prepared thereby. The crushing of such cells is implemented through the internal pressure change of the extract preparation unit 12. In order to implement this pressure change, inert gas is contained in the extract preparation unit 12, and an inert gas supply unit 16 is provided to such extract preparation unit for supplying inert gas. In other words, this inert gas supply unit 16 raises the internal pressure of the preparation unit 12 and applies pressure to the contained cells by delivering inert gas to the extract preparation unit 12. Moreover, the inert gas supplied from this inert gas supply unit 16 prevents the extract after the crushing of cells from contacting air (oxygen), and prevents the deterioration of various activities in the extract.

Furthermore, the aforementioned extract preparation unit 12 is also provided with an outlet 18 for exhausting the delivered inert gas, depressurizing the internal pressure of the preparation unit 12, and crushing (disrupturing) the cells.

The extract preparation unit 12 also comprises a control unit 20 for delivering the inert gas into the extract preparation unit 12 and controlling the pressure change pursuant to the exhaustion thereof. This control unit 20 enables the control in accordance with the strength of the film or wall covering the cells and recovers the protein synthesis activity and glycosylation activity within the extract after the crushing of cells.

Meanwhile, the translation unit 14 is connected to the extract preparation unit 12 so as to allow the extract prepared in the extract preparation unit 12 to be supplied. Although not shown in FIG. 1, a reaction container is internally provided to the translation unit 14, and the extract is injected in such reaction container. Further, the translation unit 14 also comprises a sample-injection unit, and this sample-inject unit injects the mRNA to be the substrate of protein synthesis into the reaction container.

According to the aforementioned translation device 10, a cell extract is prepared by supplying cells into the extract preparation unit 12, and crushing such cells in the extract preparation unit 12. And, the cell extract prepared thereby is supplied into the reaction container in the translation unit 14, mRNA is added thereto, and glycoprotein is synthesized thereby.

Moreover, in the foregoing translation device, if necessary, a transcription unit for producing mRNA from an expression vector may also be provided, and mRNA to be supplied to the translation device may be produced in this transcription unit. As described above, when comprising such transcription unit, the series of processes to the synthesis of protein from the expression vector via the mRNA may be automated.

EXAMPLES

Further examples of the present invention are now described in detail, but the present invention shall in no way be limited thereto.

Example 1

Preparation of Expression Vector

HIV (human immunodeficiency virus) GP120 was used as the protein known to be capable of being glycosylated, and the in-vitro synthesis of the glycoprotein thereof was attempted. In order to synthesize this glycoprotein, an expression vector for expressing this gp120mRNA was structured as follows. FIG. 2 shows a frame format of the structuring method of the expression vector, and FIG. 3 shows the structure of the gp120mRNA comprising polyhedrin UTR expressed from this expression vector. Moreover, the base sequence of this polyhedrin 5'-UTR is shown in SEQ ID NO. 1, and the base sequence of 3'-UTR is shown in SEQ ID NO. 2 (Robert, D. et al., Virology 185, 229-241 (1991)).

In FIG. 2, foremost, point mutation was inserted into the pVL1393-gp120 plasmid with PCR, and the recognition sites of Eco RI and Sal I were formed at both ends of the gp120.

The plasmid with the point mutation inserted therein was cut with restriction enzymes of Eco RI and Sal I, and the gp120' fragment with slightly chipped ends was isolated. Meanwhile, the plasmid pUC18, which is to be the frame of the expression vector, was similarly cut with restriction enzymes of Eco RI and Sal I, and the aforementioned gp120' fragment was inserted therein in order to obtain pUC18-1.

Next, two primers (both having Xho I or Sal I as a terminus) were used to amplify the remaining sequence of 3' terminal and 3'UTR sequence of gp120 from the pVL1393-gp120 plasmid with PCR, and this amplified fragment was inserted into the Sal I site of the pUC18-1 to obtain pUC18-2.

The remaining sequence of the 5' terminal and 5'UTR sequence of gp120 were produced by synthesis, and, upon this synthesis, T7RNA polymerase promoter SEQ ID NO. 3 was added to the upstream of the 5'UTR. In addition, an Eco RI site was inserted at both ends of this synthesized fragment with PCR, and this fragment was inserted into the Eco RI site of the pUC18-2. Thereby produced was a pUC18-gp120 plasmid inserted into the gp120 expression cassette containing the UTR sequence in the downstream of the T7RNA polymerase promoter sequence.

This pUC18-gp120 plasmid was transcribed in-vitro by employing MEGAscript™ (Ambion) in order to prepare the gp120mRNA shown in FIG. 3. Various examinations in the synthesis of glycoprotein were conducted with this gp120mRNA as the template.

(1) Influence of Cell Count

Insect cells Sf21 cells (J. L. Vaughn, R. H. Goodwin, G. L. Tompkins, and P. McCawley, In-vitro, 13, 213-217 (1977)) were used for the preparation of the cell extract. Cell suspensions of differing cell concentrations of the Sf21 cells were respectively inserted into a miniature bomb (MINI-BOMB CELL DISRUPTION CHAMBER (manufactured by KONTES)), and processed for 30 minutes at a nitrogen gas pressure of 8 kgf/cm$^2$. An extract was obtained by centrifuging (manufactured by BECKMAN, L7 Ultracentrifuge Type 55, Rotor: SW40Ti rotor, 14000 rpm☐15 min) the respective cell solutions after this processing.

The translation performance was examined by employing the extract prepared above. In order to analyze the translation performance, the aforementioned gp120mRNA was added to the extract such that the final concentration would be 200 μg/ml, and translational reaction was implemented thereby. The quantity of the post-reaction protein was determined with two methods. One method is a method of detecting, with avidin, the incorporated amount of the biotin-labelled lysine tRNA to the translational product. The other method is a method of detecting the translational product with the Western blotting method employing a GP120 antibody and determining the quantity of the detected product with a densitometer (FastScan, manufactured by Molecular Dynamics). The translation performance was evaluated with these determination methods. The results are shown in Table 1.

TABLE 1

| Influence of Cell Count | | | | |
| --- | --- | --- | --- | --- |
| Cell Density (10$^8$ cells/ml) | 1.5 | 1.0 | 0.5 | 0.25 |
| Translation Performance (%) | 91 | 100 | 44 | 1.7 |

As shown in Table 1, the preferable cell count for the cell extract to maintain translation performance was within the range of 0.25 to 2.5×10$^8$ cells/ml, and most preferably 1.0×10$^8$ cells/ml.

(2) Influence of Nitrogen Gas Pressure

Influence on the translation performance was examined similar to the above with the nitrogen gas pressure in the miniature bomb in a range of 2 to 14 kgf/cm$^2$. The cell count was set to 1.0×10$^8$ cells/ml, which was preferable in the aforementioned examination, and the cells were crushed by setting the nitrogen gas processing time to 30 minutes. The gp120mRNA was added to the cell extract such that the final concentration would be 200 μg/ml, and the translational reaction was implemented thereafter. The translation performance was compared from the protein synthesis amount under the respective gas pressure conditions. The results are shown in Table 2.

TABLE 2

| Influence of Nitrogen Gas Pressure | | | |
| --- | --- | --- | --- |
| Nitrogen Gas Pressure (kg/cm$^2$) | 5 | 8 | 14 |
| Translation Performance (%) | 99 | 100 | 64 |

As shown in Table 2, the nitrogen gas pressure may be set within the range of 2 to 14 kgf/cm$^2$, and preferably within the range of 5 to 8 kgf/cm$^2$, and most preferably to 8 kgf/cm$^2$.

Moreover, FIG. 4 shows the fractional pattern upon synthesizing protein from the gp120mRNA and fractionalizing the synthesized protein by employing the Sf cell extract prepared under the pressurization conditions of 5, 8 and 14 kgf/cm$^2$. As shown in lanes 2, 4 and 6 of FIG. 4, glycoprotein (shown as arrow 1 in FIG. 4) is specifically synthesized from mRNA in the cell extract prepared under the pressurization conditions of 5 to 14 kgf/cm$^2$, and, particularly, favorable glycoprotein synthesis was detected in the extract under the pressurization conditions of 8 and 14 kgf/cm$^2$.

(3) Influence of Pressurization Time by Nitrogen Gas

The nitrogen gas pressurization time for preparing the cell extract was examined by setting the cell count to 1.0×10$^8$ cells/ml and the nitrogen gas pressure to 8 kgf/cm$^2$.

TABLE 3

| Influence of Pressurization Time by Nitrogen Gas | | | | | | | | |
| --- | --- | --- | --- | --- | --- | --- | --- | --- |
| Pressurization Time (min) | 3 | 5 | 10 | 15 | 30 | 60 | 90 | 120 |
| Translation Performance (%) | 25 | 40 | 56 | 63 | 76 | 100 | 100 | 46 |

As shown in Table 3, the pressurization time would be sufficient so as long as it is 3 minutes or more, and, particularly, the preferable pressurization time was 30 to 60 minutes.

(4) Influence of Spray Velocity

The velocity of spraying the solution of the crushed cells from the miniature bomb within the range of 15 to 200 ml/sec was examined. The spray velocity did not influence the translation performance.

Example 2

Examination of Translational Reaction Conditions (1) Optimization of mRNA Concentration The additive amount of mRNA to the cell extract during the translational reaction was examined. 3.125 μg/ml to 400 μg/ml of mRNA was respectively added to the aforementioned Sf cell extract such that the concentration thereof would be sequentially doubled, and the translation performance and glycosylation performance were measured thereby. The results are shown in FIG. 5. In FIG. 5, the circle represents the GP120 without the addition of a sugar chain and the diamond represents the GP120 with the addition of a sugar chain.

As shown in FIG. 5, the production of GP120 (unglycosylated) in 200 μg/ml was high, and it has been evidenced that the translation performance could be efficiently used. Meanwhile, the glycoprotein showed an approximately stable high value when 50 μg/ml or more.

(2) Influence of Reaction Temperature and Reaction Time

Temperature conditions at the time of the translational reaction were examined. gp120mRNA was added to the cell extract such that the final concentration would be 200 μg/ml and reacted for 30, 60 and 90 minutes under a temperature of 15° C. to 45° C., and the production of the translational product was measured. Here, a cell extract prepared by crushing cells upon setting the cell count to $1.0 \times 10^8$ cells/ml and the nitrogen gas processing time to 30 minutes was used.

Figure 6:
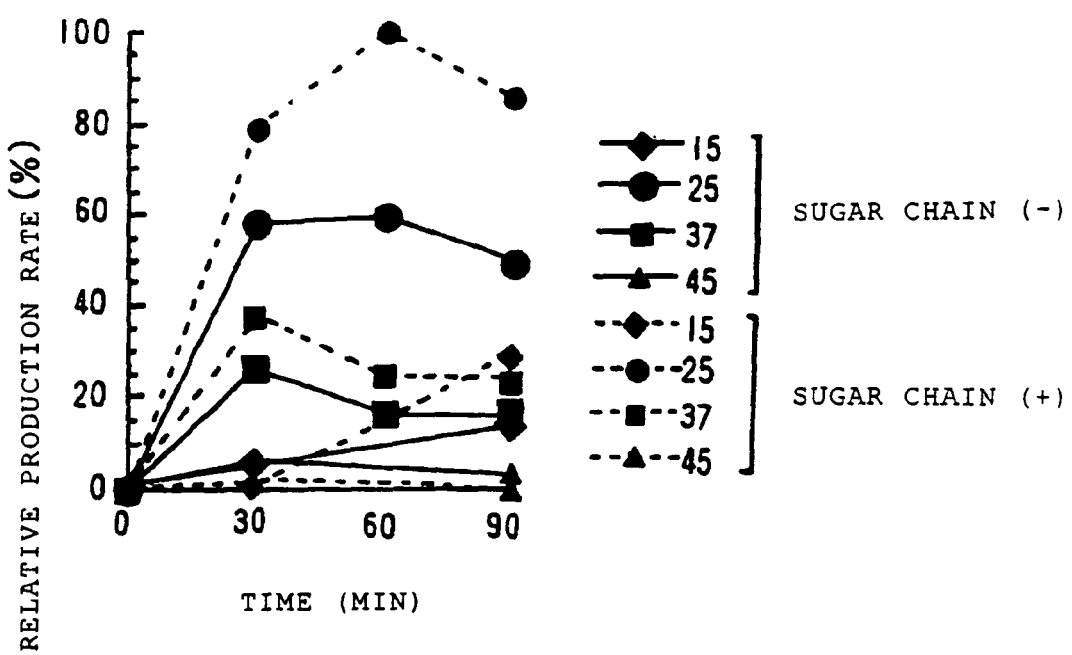
FIG. 6 is a diagram showing the examination results of a translational reaction time in Example 3.

FIG. 6 shows a graph of the relative production. As shown in FIG. 6, at a reaction temperature of 25° C., translation and glycosylation activities were yielded, and, particularly, the peak of glycosylation activity existed at a reaction time of approximately 60 minutes, and the peak of translation activity was speculated to be roughly between 30 to 60 minutes.

Meanwhile, at 37° C., in comparison to 25° C., the translation and glycosylation activities deteriorated to approximately one half, and at 45° C. both activities deteriorated significantly. Moreover, at 15° C., although both activities are low, a pattern was represented where the production increased proportionately to the time with respect to glycoprotein.

Figure 7:
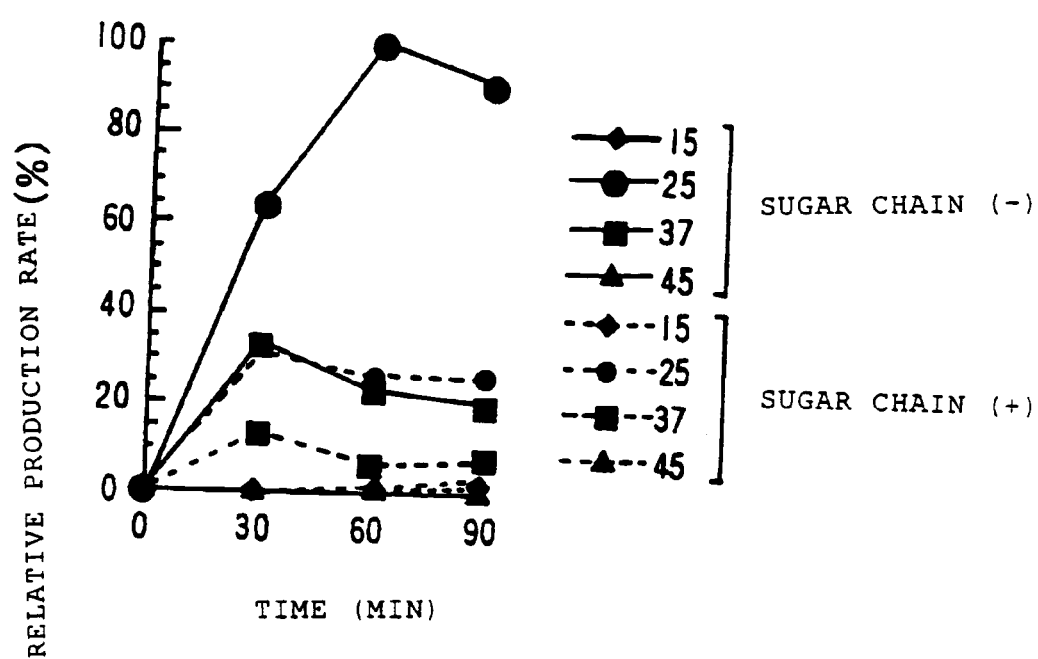
FIG. 7 is a diagram showing the examination results of a translational reaction temperature in Example 3.

Further, FIG. 7 shows a comparative graph of the production rate of GP120 with respect to the reaction temperature and reaction time by employing a purple silkworm cell extract prepared by crushing purple silkworm cells under similar conditions as with the aforementioned Sf cells. Favorable translation and glycosylation activities were also yielded at a reaction temperature of 25° C. with the purple silkworm as well.

(3) Influence of Additives such as Reagents

Influence on the translation performance upon adding various reagents to the cell extract was examined. Here, magnesium acetate, potassium acetate, spermidine, GTP, ATP and creatine kinase were respectively added at a fixed scope of concentration to the extract, and the production quantity of protein and glycoprotein from the gp120mRNA was relatively determined, and the translation performance and glycosylation performance were examined.

Figure 8:
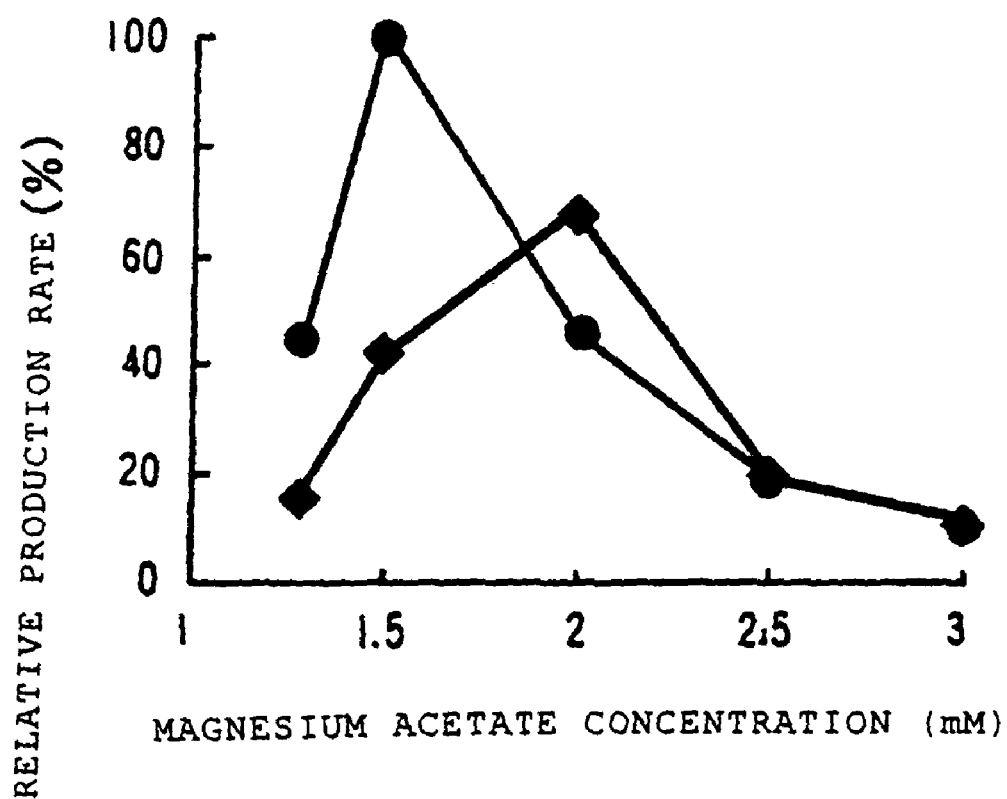
FIG. 8 is a diagram showing the examination results of the magnesium acetate concentration in Example 3.

FIG. 8 shows the examination results of the magnesium acetate concentration. In FIG. 8, the circle represents the GP120 without the addition of a sugar chain and the diamond represents the GP120 with the addition of a sugar chain.

As shown in FIG. 8, with respect to magnesium acetate, a favorable translation activity was yielded at 1.5 mM, and a favorable glycosylation activity result was represented at 2 mM.

FIG. 9 shows the examination results of the potassium acetate concentration. With respect to potassium acetate, both the translation activity and glycosylation activity were high at 100 mM. In FIG. 9 also, the circle represents the GP120 without the addition of a sugar chain and the diamond represents the GP120 with the addition of a sugar chain.

Figure 10:
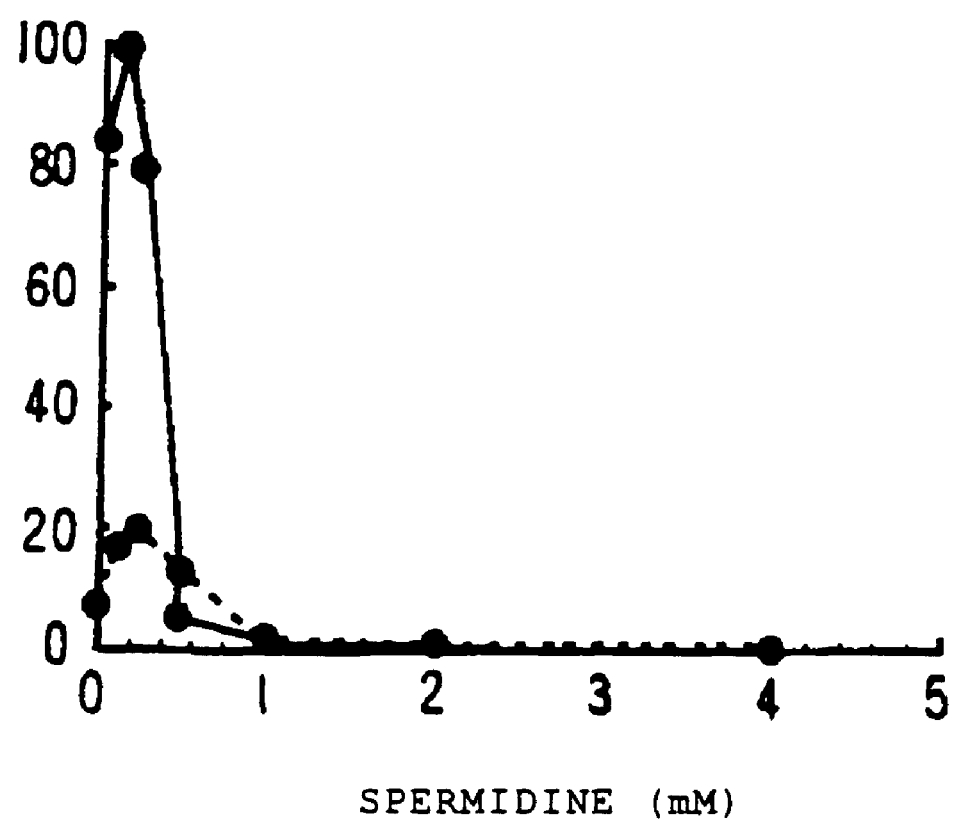
FIG. 10 is a diagram showing the examination results of the spermidine concentration in Example 3.

FIG. 10 shows the examination results of the spermidine concentration. With respect to spermidine, protein production (unglycosylated) was highest at 0.25 mM, and showed at 0.25 mM is preferable. In FIG. 10 (and FIG. 11, FIG. 12 and FIGS. 13(a) and 13(b) as well), the solid line represents an unglycosylated GP120, and the dotted line represents the glycosylated GP120.

Figure 11:
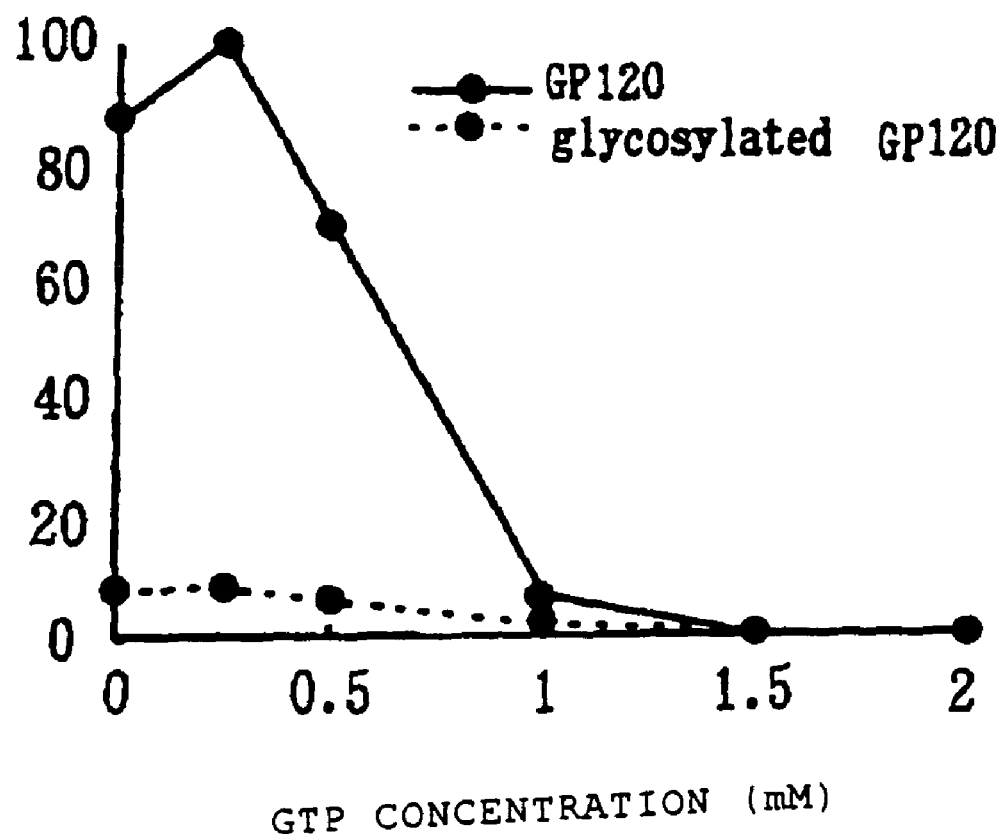
FIG. 11 is a diagram showing the examination results of the GTP concentration in Example 3.

FIG. 11 shows the examination results of the GTP concentration. With respect to GTP, protein production (unglycosylated) was highest at 0.25 mM, and translation was performed efficiently within such scope of concentration. Meanwhile, the production of glycoprotein was not influenced largely by the GTP concentration.

Figure 12:
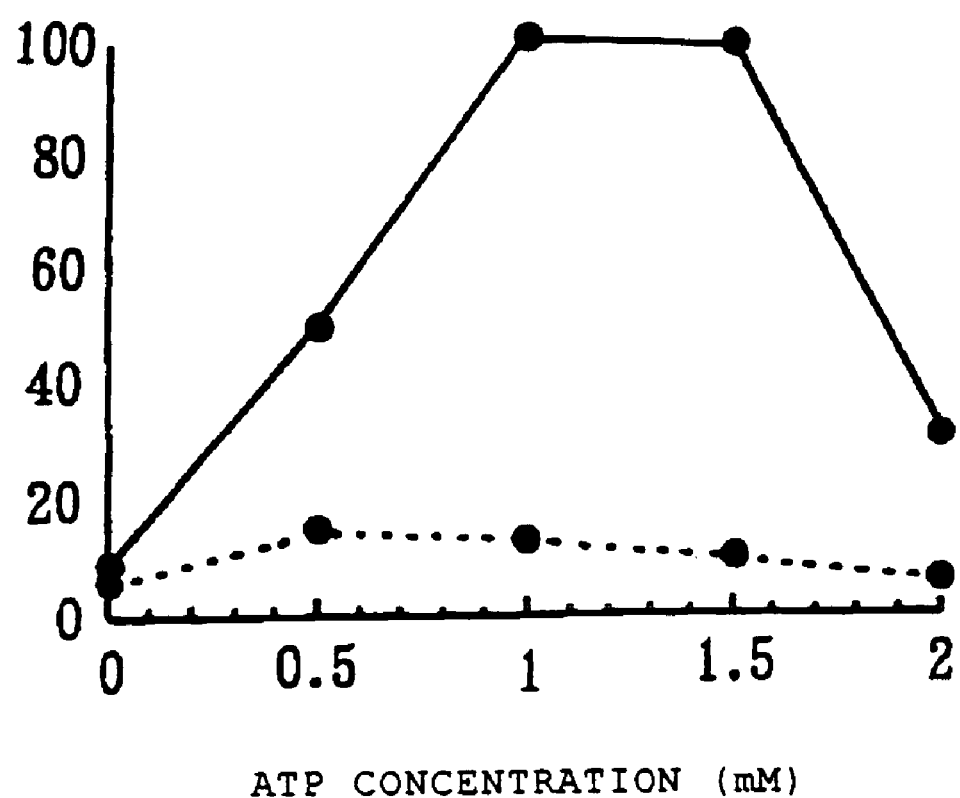
FIG. 12 is a diagram showing the examination results of the ATP concentration in Example 3.

FIG. 12 shows the examination results of the ATP concentration. With respect to ATP, protein production (unglycosylated) was highest at 1 to 1.5 mM, and translation was performed efficiently within such scope of concentration. Meanwhile, the production of glycoprotein showed a slightly high value at 0.5 mM, but was not influenced largely by the ATP concentration.

Figure 13:
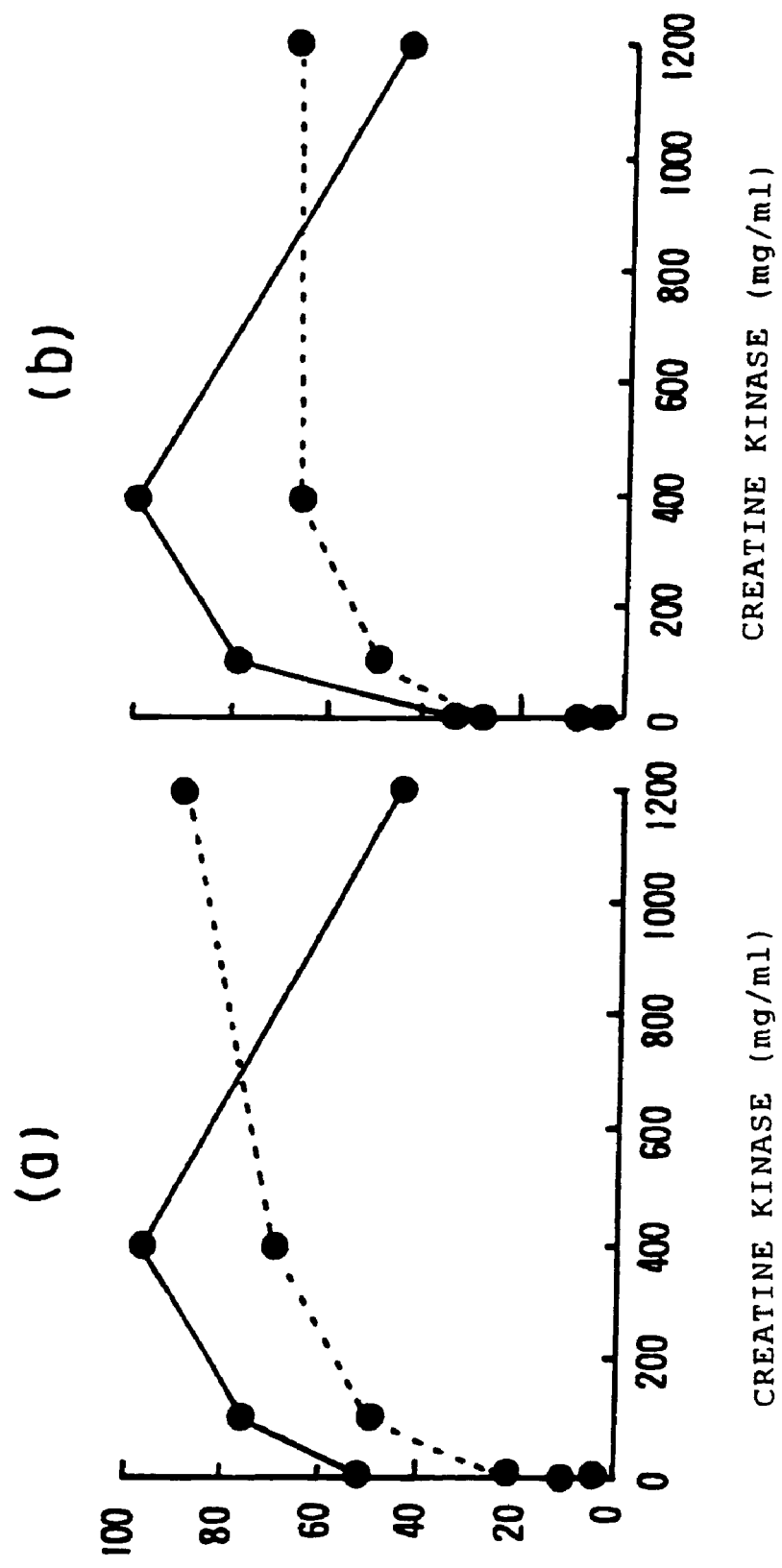
FIG. 13 is a diagram showing the examination results of the creatine kinase concentration in Example 3.

FIG. 13(a) and FIG. 13(b) show the examination results of the creatine kinase concentration. As shown in FIG. 13(a) and FIG. 13(b), the translation activity yielded the most favorable results at 400 μg/ml upon conducting two experiments. Meanwhile, the glycosylation activity yielded favorable results at 400 μg/ml or more.

These results were summarized, and a cell extract with the following composition was prepared in the Examples below, and a translational reaction was conducted at 25° C.: insect cell extract A260=30.4 HEPES-KOH (pH7.95) final concentration 10.6 mM, magnesium acetate final concentration 1.3 mM, potassium acetate final concentration 100 mM, DTT final concentration 2.5 mM, spermidine final concentration 0.25 mM, creatine kinase final concentration 444 μg/ml, creatine phosphate final concentration 8.0 mM, ATP final concentration 1.2 mM, GTP final concentration 0.25 mM, amino acid mixture final concentration 25 μMm, RNA final concentration 200 μg/ml.

Example 3

Identification of Translational Product Employing Insect Cell Extract

The translational product GP120 synthesized by employing the aforementioned cell extract was analyzed with the Western blotting method using an HIV patient antiserum. The results of the analysis are shown in FIG. 14 and FIG. 15.

Figure 14:
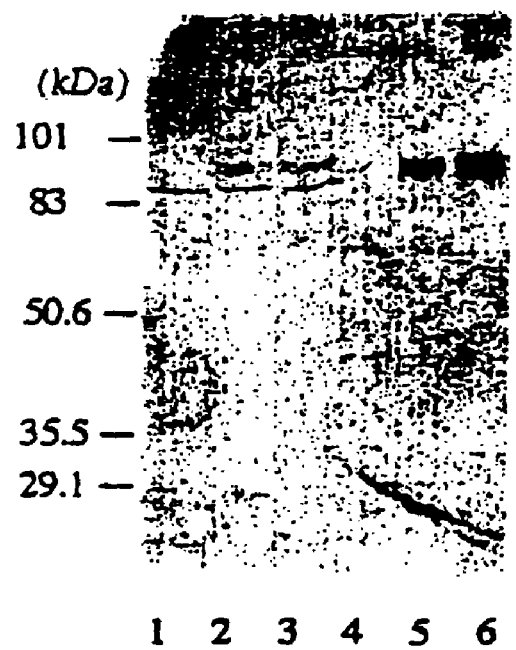
FIG. 14 is a diagram showing the results of identifying, with Western blotting, the translational product by employing the insect cell extract in Example 3.
Figure 15:
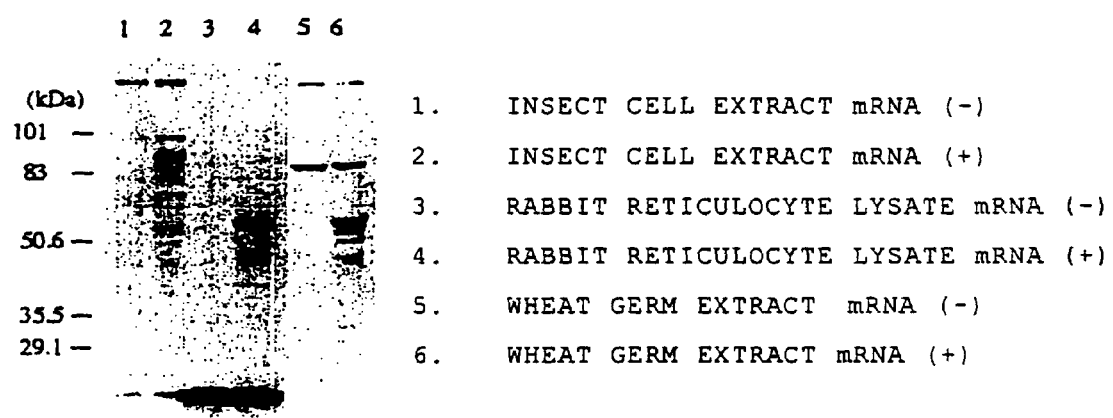
FIG. 15 is a diagram showing the results upon detecting, with Western blotting, the translational product pursuant to the cell extract of insect cells, rabbit reticulocyte and wheat germ in Example 3.

As shown in FIG. 14, GP120 was detected at a position corresponding to 90 kDa and 56 kDa on the SDS-PAGE (lane 2 and lane 3). Meanwhile, GR120 expressed pursuant to the Sf21 cells with the baculoviridae insect cells is a glycoprotein and was detected as an extremely strong band at the position of 90 kDa (lane 5 and lane 6). This suggests that glycosylation may have been performed to the translational product synthesized with the SF cell extract.

Meanwhile, the translational product obtained in the control cell extract prepared from rabbit reticulocyte and wheat germ was detected with a strong band at a position of 56 kDa (lane 4 and lane 6 in FIG. 15), and a band corresponding to the position of 90 kDa, as with the translational product synthesized with the insect cell extract (lane 2), could not be detected. This suggests a strong possibility that post-translational modification such as glycosylation was performed only to the GP120 synthesized with the insect cell extract.

Example 4

Deglycosylation of Translational Reaction Product

In order to confirm that the translational product GP120 synthesized pursuant to the translational reaction upon employing the Sf21 cell extract in Example 3 is a glycosylated glycoprotein, the translational product GP 120 was processed with saccharolytic enzymes. Here, as such saccharolytic enzymes, an N-type saccharolytic enzyme (such as N-glycosidase F, endoglycosidase F or endoglycosidase H) was used. The results of the decomposition reaction are shown in FIG. 16.

As shown in FIG. 16, as a result of processing the GP120 with the aforementioned N-type saccharolytic enzyme, the 90 kDa band existing in the unprocessed fraction disappeared, and, in place thereof, a new protein band was detected at a position unacknowledged in the unprocessed sample (position shown with the arrow). This shows that the band is a band shift produced by deglycosylation, and strongly suggests that an N-type sugar chain was added to the translational reaction product GP120. Moreover, although similar processing was performed with O-glycosidase, the addition of an O-type sugar chain could not be acknowledged (not shown).

Whether the translational product has a sugar chain was examined with other methods. The aforementioned GP120 protein was provided to a lectin-sepharose column, and fractionated by being eluted with methyl-α-D-mannopyranoside. And, Western blotting was performed to the through fraction obtained above and to the fraction eluted with methyl-α-D-mannopyranoside by employing an HIV patient antiserum. As a result, a gp120 band was detected at a position corresponding to the aforementioned 90 kDa only for the fraction eluted with methyl-α-D-mannopyranoside (not shown). Accordingly, this also strongly suggests that the translational product GP120 is a glycoprotein having a sugar chain.

Example 5

Analysis of Glycoprotein Synthesis Employing Various mRNA

With respect to control sequences (such as UTR) and signal sequences, as well as code sequences coding a protein capable of being glycosylated, mRNA differing from the foregoing Examples was prepared to examine whether translation and glycosylation would be performed. The UTR used here derived from baculoviridae polyhedrin or from a bovine growth hormone (BGH). Moreover, the signal sequence used here derived from interleukin 6 (IL6) (SEQ ID NO. 6) or from chicken lysozyme (cL) (SEQ ID NO. 4). Further, as the code sequence, an interleukin 6 (IL6) code sequence was used as the common sequence. Similar to Example 1, these were structured as an expression plasmid by employing pUC18, and mRNA was produced thereby to examine the following translation and glycosylation activities. The results are listed in Table 4.

TABLE 4

|   |   |   |   |   | Translation/Glycosylation | Insects | Purple Silkworm | Rabbit | Wheat Germs |
|---|---|---|---|---|---|---|---|---|---|
| 1 |   | BMV Protein 2a |   |   | Translation | + | + | ++ + | + |
| 2 |   | Protein 2a |   |   | Translation | ± | ± | ++ ++ | ++ |
| 3 |   | Exterior Covering Protein |   |   | Translation | + | + | ± ++ | ++ |
| 4 |   | SF162 gp120 |   |   | Translation | + | + | + | + |
|   |   |   |   |   | Glycosylation | + | + | − | − |

| Expression System | 5'-UTR | Signal | Code Protein | 3'-UTR |   |   |   |   |   |
|---|---|---|---|---|---|---|---|---|---|
| 5 ppILIL6p | Polyhedrin | IL6 | IL6 | Polyhedrin | Translation | − | ND | − | ND |
| 6 ppCIL6p | Polyhedrin | cL[a] | IL6 | Polyhedrin | Translation | + | + | + | ND |
|   |   |   |   |   | Glycosylation | + | + |   | ND |
| 7 pp(−)IL6p | Polyhedrin | None | IL6 | Polyhedrin | Translation | + | + | + | ND |
| 8 pBILIL6B | BGH[b] | IL6 | IL6 | BGH | Translation | − | ND | − | ND |
| 9 pBCIL6B | BGH | cL | IL6 | BGH | Translation | − | ND | ± | ND |
| 10 pB(−)IL6B | BGH | None | IL6 | BGH | Translation | − | ND | ± | ND |
| 11 ppCIL6B | Polyhedrin | cL | IL6 | BGH | Translation | + | ND | + | ND |
|   |   |   |   |   | Glycosylation | + | ND |   | ND |
| 12 pBCIL6p | BGH | cL | IL6 | Polyhedrin | Translation | − | ND | − | ND |

[a]cL: chicken lysozyme
[b]BGH: bovine growth hormone
[c]ND: not determined

With the analysis employing the mRNA of SF162gp120 shown in Example 1, although the translation activity and glycosylation activity were confirmed in extracts deriving from insect SF cells or purple silkworm, in the cell extracts deriving from rabbit reticulocyte and wheat germ, translation activity was acknowledged, but glycosylation activity could be not detected.

Moreover, from the analysis employing mRNA having variously differing control sequences (row 5 to row 12), it has been exhibited that translation and glycosylation are conducted when employing a 5'UTR deriving from polyhedrin as the 5'UTR, and when employing a sequence deriving from cL as the signal sequence (row 6 and row 11). Further, glycosylation was performed in the 3'UTR regardless of it deriving from polyhedrin or from a bovine growth hormone.

Meanwhile, when employing the type deriving from BGH as the 5'UTR in the insect cell extract, and when employing an IL6 signal as the signal sequence, only translation was conducted, and glycosylation was not performed. From this, it is clear that the 5'UTR and signal sequence are important in the implementation of glycosylation.

In addition, with respect to cell extracts deriving from rabbit reticulocyte and wheat germ, which are controls, glycosylation could not be observed at all in the employed mRNA.

Example 7

Examination Employing CHO Cells

Similar to the aforementioned insect cells, examined was whether the cell extracts of mammalian cells have both translation and glycosylation activities. Here, CHO cells were used as the mammalian cells, and a CHO cell extract was prepared with the same method as the preparation conditions of the cell extract of the foregoing insect cells. Moreover, pursuant to the analysis of the translation performance (and other such factors) of the extract of CHO cells, three types of mRNA were prepared. These mRNA are, as shown in the following Table 5, (1) a first mRNA having a gp120 (deriving from HIV-1 SF162) code sequence, polyhedrin UTR and gp120 signal sequence, (2) a second mRNA having an IL6 code sequence, polyhedrin UTR and cL signal sequence, and (3) a third mRNA having an IL6 code sequence, mammalian expression vector pRc/CMV UTR and an IL signal sequence.

The translation activity and glycosylation activity of the CHO cell extract were examined by employing these three types of mRNA. The results are shown in Table 5. The results in the extract of insect cells (Sf cells), in which the translation and glycosylation activities were confirmed, are also shown as the positive control.

compositional solution was prepared by mixing the CHO cell extract and insect cell extract in various mixture ratios, and the translation activity and glycosylation activity pursuant to this compositional solution were examined.

Specifically, in the examination described above, used as the mRNA was IL6mRNA (mRNA from ppILIL6p, ppILIL6B or ppCLIL6B in Example 6) comprising a signal sequence deriving from IL6 or deriving from chicken lysozyme (cL). Such mRNA was added to the respective compositional solutions, and a part of such compositional solution was fractionalized pursuant to electrophoresis, and, after such fractionalization, the identification and production of the IL6 protein were compared with Western blotting employing an anti-IL6 antibody. The results of Western blotting are shown in FIG. 17, and the values in which the band strength was quantified with a densitometer are shown in Table 6.

TABLE 5

| Cell Extract | Template | Template Type | UTR | Signal Sequence | Translation | Glycosylation |
|---|---|---|---|---|---|---|
| Insect Cell | gp120 of HIV-1 SF162 | Baculoviridae (insect) | Polyhedrin | gp120 of HIV-1 SF162 | +++ | +++ |
|  | Human Interleukin 6 | CHO Cell (mammal) | Polyhedrin | Chicken Lysozyme | +++ | +++ |
|  |  |  | UTR of Mammalian Expression Vector pRc/CMV | Human Interleukin 6 | ++ | ++ |
| CHO Cell | gp120 of HIV-1 SF162 | Baculoviridae (insect) | Polyhedrin | gp120 of HIV-1 SF162 | ++ | − |
|  | Human Interleukin 6 | CHO Cell (mammal) | Polyhedrin | Chicken Lysozyme | ++ | − |
|  |  |  | UTR of Mammalian Expression Vector pRc/CMV | Human Interleukin 6 | +++ | − |

+: Synthesized    −: Not Synthesized

As shown in Table 5, with the CHO cell extract, translation activity was confirmed in each mRNA, but glycosylation activity could not be confirmed. Thus, with the CHO cell extract, although the glycosylation activity could not be confirmed, it has been shown that it is possible to recover at least an extract having a translation activity from the mammalian cells with the cell-crushing method employing the aforementioned gas pressure change.

Furthermore, upon comparing the translation performance, it has been shown that the translation performance improved when employing a pRc/CMV UTR. This implies that the correspondence of the type of prepared cell and the type of cell deriving from the UTR are important in improving the translation performance.

Meanwhile, with the insect cell extract employed as the positive control, translation activity and glycosylation activity were confirmed in each mRNA. Particularly, it has been shown that the translation activity and glycosylation activity can be improved when employing a polyhedrin UTR. From this, it is clear that a UTR deriving from living organisms capable of infecting, and being grown and developed from, the cells used to prepare the cell extract may be preferably used as the control sequence for performing translation and glycosylation upon employing such extracts.

Example 7

Mixed Compositional Solution of CHO Cell Extract and Insect Cell (Sf Cell) Extract As described above, with the CHO cell extract, translation activity was detected, but glycosylation activity could not be detected. In order to supplement this glycosylation activity, a

TABLE 6

| A) Employment of IL6 Original Signal Sequence | | | | | |
|---|---|---|---|---|---|
| CHO Cell Extract | 10 | 9.9 | 9 | 5 | 0 |
| Insect Cell Extract | 0 | 0.1 | 1 | 5 | 10 |
| pre-IL6 | 66 | 65 | 57 | 85 | 100 |
| Glycosylated IL6 | 0 | 0 | 4 | 43 | 95 |
| IL6 with Signals Removed | 0 | 0 | 3 | 6 | 33 |
| B) Replacement of IL Signal Sequence with Chicken Lysozyme Signal Sequence | | | | | |
| CHO Cell Extract | 10 | 9.9 | 9 | 1 | 0 |
| Insect Cell Extract | 0 | 0.1 | 1 | 9 | 10 |
| pre-IL6 | 26 | 29 | 23 | 31 | 48 |
| Glycosylated IL6 | 0 | 2 | 11 | 61 | 100 |
| IL6 with Signals Removed | 0 | 0 | 2 | 13 | 32 |

As shown in FIG. 17 and Table 6, with the CHO-insect (9.9:0.1) compositional solution, although an IL6 protein was detected, a glycosylated IL6 protein could not be detected. It has been shown that the glycosylation activity was not supplemented.

Meanwhile, with the CHO-insect (9:1) compositional solution and CHO-insect (5:5) compositional solution, a band was detected at a position corresponding to an IL6 protein in which a sugar chain was detected in an independent control cell extract. It has been shown that glycosylation was performed.

As described above, even with cell extracts only having a translation activity, it is possible to supplement a glycosylation activity by mixing another cell extract having glycosylation performance. For example, although the extract of CHO cells is prepared under gentle conditions of gas pressure change, one of the factors responsible for the glycosylation activity originally possessed by the cells is insufficient in yielding such glycosylation activity in the extract. However, supplementing such factor with the insect cell extract can yield the desired glycosylation activity.

Example 9

Application

With the extract (and compositional solution containing such extract) of the insect cells shown in the foregoing examples, it has been shown that translation, glycosylation and even processing could be performed in-vitro. Further, the control sequence capable of improving the efficiency of glycosylation was also demonstrated. By packing an expression vector comprising such a cell extract and control sequence, an in-vitro glycoprotein synthesis kit may be formed thereby, and it is thereby possible to easily synthesize in-vitro glycoprotein and processed protein.

Further, with the aforementioned CHO-insect compositional solution, since processing could also be performed, this compositional solution is expected to be useful as a model system for analyzing the processing of post-translational protein. In other words, by crushing the cells under a gentle condition employing inert gas, it has been suggested that a cell-free extract can be recovered while preserving the membrane relating to glycosylation or the like. Accordingly, not only is this cell-free extract useful upon synthesizing glycoprotein and the like, it is also beneficial as a model system upon analyzing how the protein (or precursor) synthesized by translation is processed after such translation.

As described above, according to the present invention, a novel cell extract preparation is provided, and it is thereby possible to easily recover a cell-free extract having translation and glycosylation functions from cells. Moreover, by employing the cell-free extract of the present invention, a desired sugar chain existing in animals and plants may be added to, for example, a recombinant protein.

What is claimed is:

1. A cell-free extract made from insects, comprising:
a cell-free extract produced by a glycoprotein synthesis system comprising
a DNA encoding a protein capable of being glycosylated;
an mRNA synthesized from the DNA;
glycoprotein synthesizing means for producing the cell extract from a cell, the cell extract having a translation activity for synthesizing the protein and a glycosylation activity for glycosylating the synthesized protein; and
synthesizing glycoprotein from the cell extract and the mRNA, wherein the glycoprotein synthesizing means comprises:
a first member for housing the cell, and preparing a cell-free extract from the cell;
a second member for providing inert gas to the first member;
a third member for delivering the inert gas to the first member, and adjusting pressure in the first member;
a fourth member for exhausting the inert gas from the first member; and
a fifth member connected to the first member, wherein the cell-free extract is provided from the first member, and the mRNA is applied to the cell-free extract,
wherein the third member provides the inert gas from the second member to the first member, applies pressure to the first member by delivering the inert gas, and then rapidly depressurizes the first member in the pressurized condition by exhausting the inert gas in the first member from the fourth member,
wherein the first member prepares the cell-free extract by crushing the cell, and provides the cell-free extract to the fifth member, and
wherein the fifth member synthesizes the glycoprotein from the cell-free extract and the mRNA,
the cell-free extract having a protein synthesis activity for synthesizing protein from RNA, the cell-free extract including an mRNA as a template for translation, an expression vector containing template DNA as a substrate for mRNA synthesis, and a promoter, wherein untranslated region sequences are provided at both ends of the expression vector, and a glycosylation activity for adding a sugar chain to the synthesized protein, and the cell-free extract having biochemical properties of:
having a protein synthesis reaction and a glycosylation reaction each at a temperature of about 15° C. to about 37° C.,
wherein the protein synthesis reaction and the glycosylation reaction are influenced by additives,
wherein the additives are magnesium acetate, potassium acetate, GTP, ATP, spermidine, and creatine kinase,
each additive has an optimal concentration range for both the protein synthesis reaction and the glycosylation reaction,
the optimal concentration range for each additive is determined by adding each additive one at a time to the cell free extract, and
the optimal concentration range for each additive being:
1 mM to 2.5 mM for magnesium acetate;
50 mM to 150 mM for potassium acetate;
1 mM or less for GTP;
0.5 mM to 2.0 mM for ATP;
0.25 mM or less for spermidine; and
1200 µg/ml or less for creatine kinase.

* * * * *

SEQUENCE LISTING

<160> NUMBER OF SEQ ID NOS: 7

<210> SEQ ID NO 1
<211> LENGTH: 52
<212> TYPE: DNA
<213> ORGANISM: Baculoviridae

<400> SEQUENCE: 1
gggagtattt tactgttttc gtaacagttt tgtaataaaa aaacctataa at                52

<210> SEQ ID NO 2
<211> LENGTH: 379
<212> TYPE: DNA
<213> ORGANISM: Baculoviridae

<400> SEQUENCE: 2
aacacgatac attgttatta gtacatttat taagcgctag attctgtgcg ttgttgattt        60
acagacaatt gttgtacgta ttttaataat tcattaaatt tataatcttt agggtggtat       120
gttagagcga aaatcaaatg attttcagcg tctttatatc tgaatttaaa tattaaatcc       180
tcaatagatt tgtaaaatag gtttcgatta gtttcaaaca agggttgttt ttccgaaccg       240
atggctggac tatctaatgg attttcgctc aacgccacaa aacttgccaa atcttgtagc       300
agcaatctag ctttgtcgat attcgtttgt gttttgtttt gtaataaagg ttcgacgtcg       360
ttcaaaatat tatgctgca                                                    379

<210> SEQ ID NO 3
<211> LENGTH: 21
<212> TYPE: DNA
<213> ORGANISM: Artificial sequence
<220> FEATURE:
<223> OTHER INFORMATION: Designed DNA to serve as T7 RNA polymerase
      promoter

<400> SEQUENCE: 3
taatacgact cactataggg a                                                  21

<210> SEQ ID NO 4
<211> LENGTH: 54
<212> TYPE: DNA
<213> ORGANISM: Artificial sequence
<220> FEATURE:

```
<223> OTHER INFORMATION: Designed DNA to serve as signal sequence to
      examine whether translation and glycosylation would be performed
<220> FEATURE:
<221> NAME/KEY: CDS
<222> LOCATION: (1)..(54)

<400> SEQUENCE: 4 atg agg tct ttg cta atc ttg gtg ctt tgc ttc ctg ccc ctg gct gct     48
Met Arg Ser Leu Leu Ile Leu Val Leu Cys Phe Leu Pro Leu Ala Ala
1               5                   10                  15 ctg ggg                                                             54
Leu Gly

<210> SEQ ID NO 5
<211> LENGTH: 18
<212> TYPE: PRT
<213> ORGANISM: Artificial sequence
<220> FEATURE:
<223> OTHER INFORMATION: Amino acid sequence resulting from translation
      of DNA SEQ ID NO. 4, above.

<400> SEQUENCE: 5

Met Arg Ser Leu Leu Ile Leu Val Leu Cys Phe Leu Pro Leu Ala Ala
1               5                   10                  15

Leu Gly

<210> SEQ ID NO 6
<211> LENGTH: 84
<212> TYPE: DNA
<213> ORGANISM: Artificial sequence
<220> FEATURE:
<223> OTHER INFORMATION: Designed DNA to serve as signal sequence to
      examine whether translation and glycosylation would be performed
<220> FEATURE:
<221> NAME/KEY: CDS
<222> LOCATION: (1)..(84)

<400> SEQUENCE: 6 atg aac tcc ttc tcc aca agc gcc ttc ggt cca gtt gcc ttc tcc ctg     48
Met Asn Ser Phe Ser Thr Ser Ala Phe Gly Pro Val Ala Phe Ser Leu
1               5                   10                  15 ggg ctg ctc ctg gtg ttg cct gct gcc ttc cct gcc                     84
Gly Leu Leu Leu Val Leu Pro Ala Ala Phe Pro Ala
                20                  25

<210> SEQ ID NO 7
<211> LENGTH: 28
<212> TYPE: PRT
<213> ORGANISM: Artificial sequence
<220> FEATURE:
<223> OTHER INFORMATION: Amino acid sequence resulting from translation
      of DNA SEQ ID NO. 6, above.

<400> SEQUENCE: 7

Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala
                20                  25
```